US00PP36149P2

(12) United States Plant Patent
Smit

(10) Patent No.: US PP36,149 P2
(45) Date of Patent: Sep. 24, 2024

(54) ***BEGONIA* PLANT NAMED 'EC-BEGO-2305'**

(50) Latin Name: *Begonia maculata*
Varietal Denomination: EC-BEGO-2305

(71) Applicant: Eden Collection, BV, Sappemeer (NL)

(72) Inventor: Obed Jacob Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 18/387,381

(22) Filed: Nov. 6, 2023

(51) Int. Cl.
*A01H 5/02* (2018.01)
*A01H 6/18* (2018.01)

(52) U.S. Cl.
USPC ..... Plt./343

(58) Field of Classification Search
USPC ..... Plt./343

CPC ... A01H 5/02; A01H 5/12; A01H 5/00; A01H 6/185; A01H 6/18
See application file for complete search history.

(56) References Cited

PUBLICATIONS

Mazo et al. Two new species of *Begonia* (section Petermannia, Begoniaceae) from Zamboanga Peninsula, Philippines with notes on an amended description of B. elatostematoides, Taiwania 67(3): 441-449, 2022. (Year: 2022).*

* cited by examiner

*Primary Examiner* — June Hwu
(74) *Attorney, Agent, or Firm* — Cassandra Bright

(57) ABSTRACT

A new and distinct cultivar of *Begonia* plant named 'EC-BEGO-2305' is disclosed, characterized by large dark green leaves with green-white dots. Plants have broad, spreading, semi-upright habits, and flower from spring to autumn. The new variety is a *Begonia*, typically used as an ornamental plant.

3 Drawing Sheets

Latin name of the genus and species: *Begonia maculata*.
Variety denomination: 'EC-BEGO-2305'.

BACKGROUND OF THE INVENTION

The new cultivar is a product of a planned breeding program to produce distinct and better performing *Begonia* varieties. The new variety was selected as a seedling resulting from the crossing made by the inventor, Obed J. Smit, a citizen of the Netherlands, in 2018. The seed parent is the unpatented *Begonia maculata* '180018', a variety from the inventor's breeding line. The pollen parent is an unnamed, unpatented specimen of *Begonia maculata*. The new variety was selected by the inventor in 2018 at a commercial greenhouse in Sappemeer, the Netherlands.

Asexual reproduction of the new cultivar 'EC-BEGO-2305' by terminal cuttings was first performed in Sappemeer, the Netherlands at a commercial greenhouse in March 2021, and has shown that the unique features of this cultivar are stable and reproduced true to type through successive generations.

SUMMARY OF THE INVENTION

The cultivar 'EC-BEGO-2305' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-BEGO-2305'. These characteristics in combination distinguish 'EC-BEGO-2305' as a new and distinct *Begonia* cultivar:

1. Large leaves.
2. Large dots on leaves.
3. Very strong stems.

PARENT COMPARISONS

Plants of the new cultivar 'EC-BEGO-2305' are similar to plants of the female parent in most horticultural characteristics, however, plants of the new cultivar 'EC-BEGO-2305' differ from in the following characteristics:

1. Leaves of the new variety have large dots, while leaves of the seed parent have small dots.
2. Leaves of the new variety have fewer dots than leaves of the seed parent.
3. Leaf underside of the new variety is colored greyed-red with a green margin, while leaf underside of the seed parent is green.

Plants of the new cultivar 'EC-BEGO-2305' are similar to plants of the male parent in most horticultural characteristics, however, plants of the new cultivar 'EC-BEGO-2305' differ in the following characteristics:

1. Leaves of the new variety are larger than leaves of the pollen parent.
2. Leaf underside of the new variety is colored greyed-red with a green margin, while leaf underside of the pollen parent is red.

COMMERCIAL COMPARISONS

Plants of the new cultivar 'EC-BEGO-2305' are similar to plants of the commercial variety *Begonia* 'Double Dot', unpatented. However, plants of the new cultivar differ in the following characteristics:

1. Leaf color of the new variety is darker green than leaf color of this comparator.
2. Leaves of the new variety have large green-white dots, while leaves of this comparator have small white dots.
3. Leaves of the new variety have fewer dots than leaves of this comparator.
4. Leaf underside of the new variety is colored greyed-red with a green margin, while leaf underside of this comparator is green.

Plants of the new cultivar 'EC-BEGO-2305' are similar to plants of co-pending U.S. Plant patent application Ser. No. 18/387,372, 'EC-BEGO-2304'. However, plants of the new cultivar differ in the following characteristics:

1. Leaf color of the new variety is dark green with green-white dots, while the leaf color of this comparator is darker green with silvery-white dots.
2. Leaf underside of the new variety is colored greyed-red with a green margin, while leaf underside of this comparator is dark red.
3. Leaves of the new variety are slightly curved with a margin having shallow, irregular crenations in lower ⅔, entire upper ⅓, while leaves of this comparator are curved with a toothed rim.
4. Leaves of the new variety are larger than leaves of this comparator.
5. Leaves of the new variety are not glossy, while leaves of this comparator are glossy.

BRIEF DESCRIPTION OF THE PHOTOGRAPHS

The accompanying photograph in FIG. 1 illustrates in full color a typical plant of 'EC-BEGO-2305' grown in a greenhouse. The plant is approximately 30 weeks of age.

Figure 1:
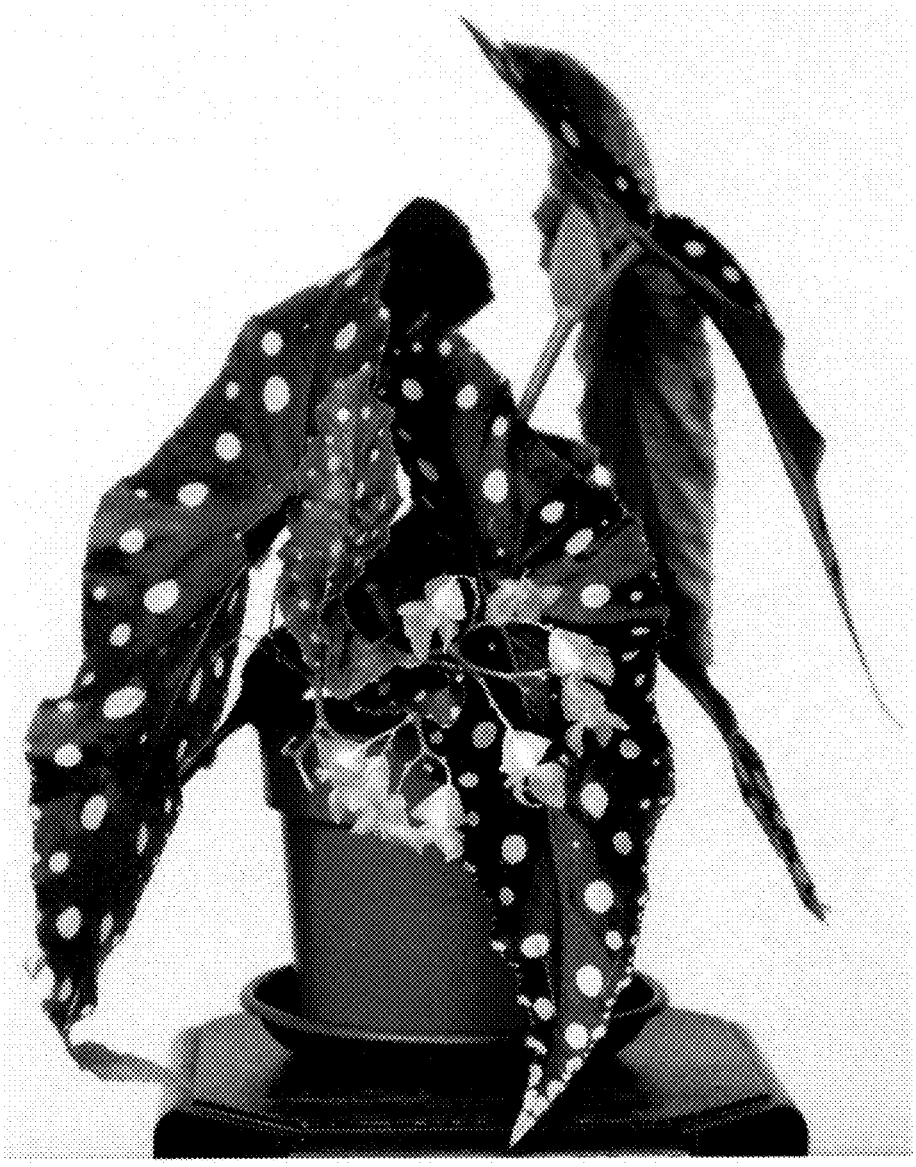
Figure 2:
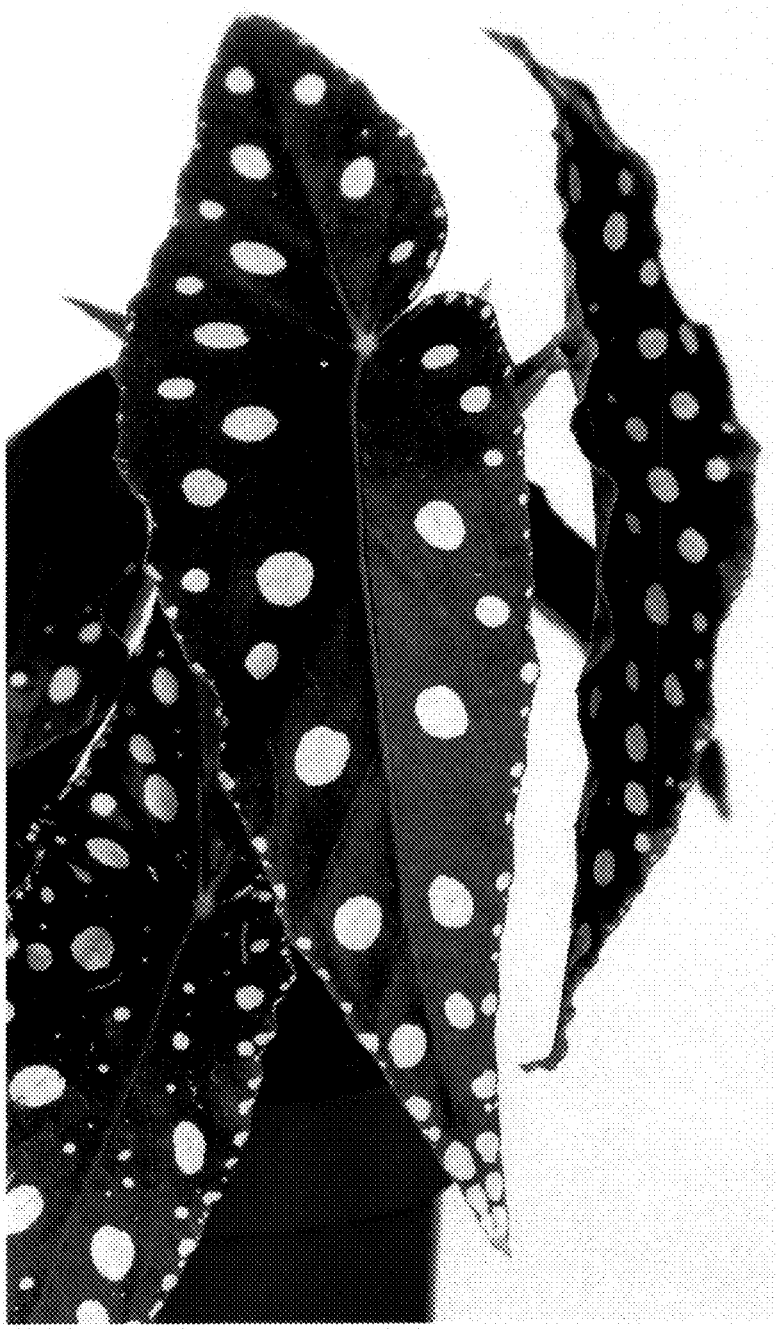
FIG. 2 illustrates a close up of the foliage.
Figure 3:
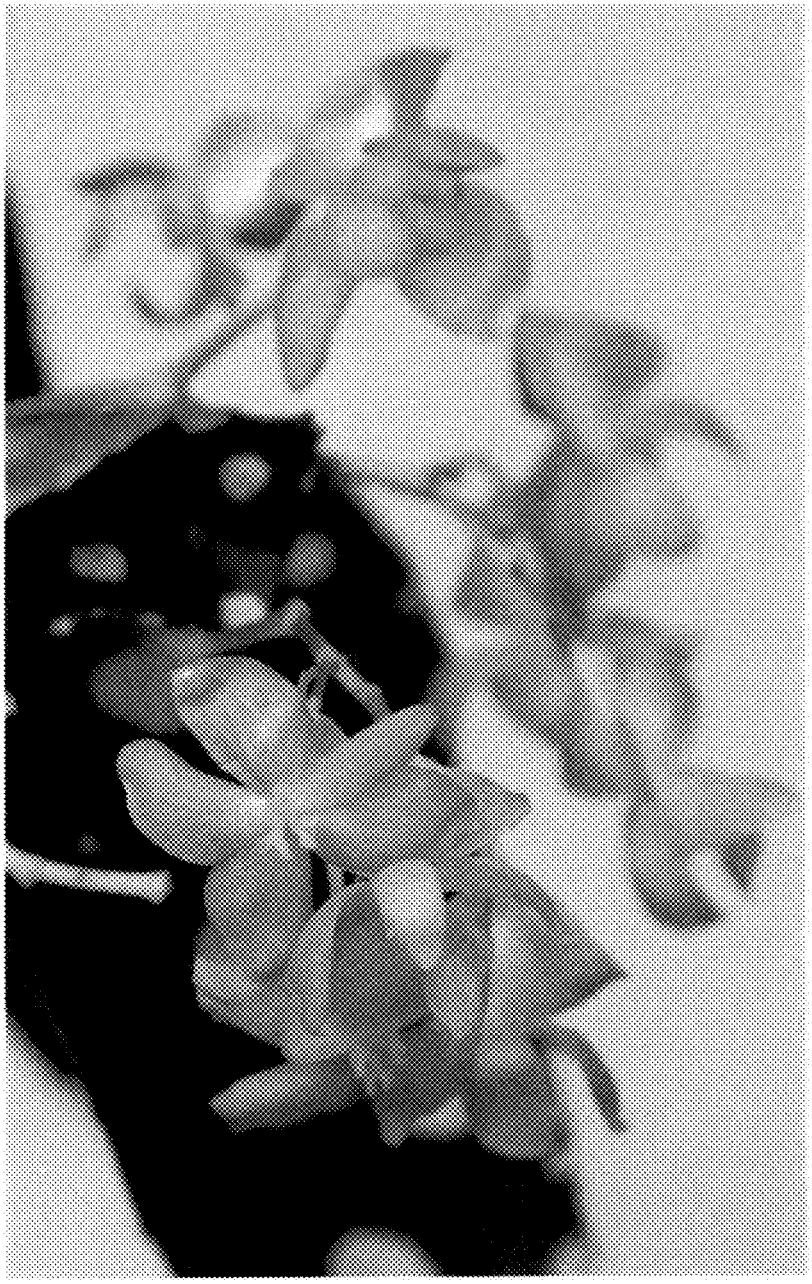
FIG. 3 illustrates flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-BEGO-2305' plants at 14 weeks of age, grown in a greenhouse in Sappemeer, the Netherlands during October. The growing temperature ranged from 16° C. to 20° C. at night to 18° C. to 20° C. during the day. Measurements and numerical values represent averages of typical flowering types.

Botanical classification: *Begonia maculata* 'EC-BEGO-2305'.

PROPAGATION

Time to initiate roots: About 21 days at approximately 21° C. in summer.

Time to produce rooted cutting: About 28 days at 21° C. in summer.

Description of roots: Fibrous, fine, moderately dense, freely branching. White in color, not accurately measured with R.H.S. chart.

PLANT

Plant type: Perennial potted plant.
Plant shape: Broad ovate.
Growth habit: Broad spreading-semi-upright.
Plant spread: Average 41 cm.
Height: Average 32.7 cm to top of foliar plane; 11 cm to top of floral plane.
Growth rate: Moderate.
Plant vigor: Moderate.
Age of plant described: Approximately 14 weeks from placing unrooted cuttings in the pots.
Branching habit: Moderately free branching, basal branches only.
Pinching: Pinching not required.
Number of primary (main) branches per plant: Average 2.
Number of secondary (lateral) branches per plant: None.
Main branches:
*Length*.—Average 17.1 cm.
*Diameter*.—Average 0.8 cm.
Internode length: Average 7.1 cm.
Appearance and shape: Smooth, glabrous.
Luster: Moderately glossy.
Aspect: Average 15°.
Strength: Very strong.
Color:
*Developing*.—RHS Yellow-Green 146B.
*Mature*.—RHS Yellow-Green 146A.
*At internodes*.—RHS Grey-Brown 199B and 199C.
Pubescence: None.
Lenticels:
*Length*.—0.15 cm.
*Width*.—0.5 mm.
*Shape*.—Linear.
*Color*.—RHS Yellow-Green 147D.
Other: Stems slightly zigzag, typical for many *Begonia* varieties.

FOLIAGE

Leaf:
*Arrangement*.—Alternate, single.
*Quantity*.—Average 12.
*Average length*.—38.7 cm.
*Average width*.—12.1 cm.
*Shape of blade*.—Obliquely lanceolate.
*Apex*.—Narrow acute.
*Base*.—Oblique, lobes slightly overlapping.
*Margin*.—Shallow, irregular crenations in lower ⅔, entire upper ⅓, weakly undulate.
*Texture of top surface*.—Velvety.
*Texture of bottom surface*.—Velvety.
*Pubescence*.—None.
*Luster, upper side*.—Very slightly glossy.
*Luster, under side*.—Slightly to moderately glossy.
*Rugosity, upper side*.—Non-rugose.
*Rugosity, under side*.—Non-rugose.
*Color*.—Young foliage upper side: RHS Yellow-Green 146A, moderately dotted with circular dots, average diameter: 0.6 cm, dots near the leaf margins smaller, average diameter: 0.2 cm, all dots colored Greyed-Green 190C to 190D, with a strong silvery-velvety shine. Young foliage under side: RHS Yellow-Green 148A, veined Greyed-Orange 175A, lamina moderately dotted with circular dots, average diameter: 0.6 cm, dots near the leaf margins smaller, average diameter: 0.2 cm, all dots colored Yellow-Green 144A and 144B. Mature foliage upper side: RHS Greyed-Green N189A, moderately dotted with broad elliptic dots, average length: 1.4 cm, average width: 0.9 cm, dots near the leaf margins smaller average length: 0.7 cm, average width: 0.4 cm, all dots colored Greyed-Green 188C and 188D, with a strong silvery-velvety shine. Mature foliage under side: RHS Greyed-Purple 183A with Green 137C margin.

*Venation*.—Pattern: Palmate-pinnate. Venation color upper side: RHS Yellow-Green 143A. Venation color under side: RHS Greyed-Purple 183A.

*Petiole*.—Length: Average 4.8 cm. Diameter: Average 0.6 cm. Texture: Glabrous, smooth. Luster: Moderately glossy. Strength: Low to moderate. Color, upper side: RHS Yellow-Green 144A and 146B. Color, under side: RHS Yellow-Green 144A and 146B.

*Stipules*.—Quantity: 2 leafy stipules present at the base. Shape: Ovate. Average Length: 5.6 cm. Average width: 3.2 cm. Apex: Abruptly acute. Base: Broad cuneate. Margin: Entire. Color: Both sides colored RHS Yellow-Green 144A, fading to 145A and 145B.

FLOWER

Inflorescence:

*Type and form*.—Panicle.
*Height*.—Average: 18.3 cm (including peduncle).
*Diameter*.—Average: 20 cm.
*Quantity of flowers per inflorescence*.—Average 26.
*Quantity of inflorescences per plant*.—Typically 1.
*Quantity of flower buds per inflorescence*.—Average 6.
*Natural flowering season*.—Spring to autumn.
*Time to flower*.—14 to 20 weeks after potting cuttings.

Flower bud:

*Length*.—2.6 cm.
*Diameter*.—1.5 cm.
*Shape*.—Ovate.
*Texture*.—Glabrous, slightly velvety.
*Luster*.—Matte.
*Color*.—RHS Red 55A and 55B, immature ovary Yellow-Green 145B.

Flower:

*Type and form*.—Female flowers only, rotate, single.
*Aspect*.—Outward to nodding.
*Flowering habit*.—Moderately.
*Fragrance*.—None.
*Shape*.—Rotate, single.
*Height*.—Average: 3.3 cm.
*Diameter*.—Average: 3.3 cm.
*Length*.—Average: 2.8 cm.
*Longevity on plant*.—Average 10 days.
*Persistence*.—Self-cleaning.

Tepals:

*Arrangement*.—Rotate.
*Quantity per flower*.—Average 5.
*Number of whorls*.—Average 2.
*Shape*.—Outer: Elliptic. Inner: Narrow elliptic to narrow oblong.
*Length* (*inner and outer tepals*).—Average 2.1 cm.
*Width*.—Outer: Average 1.3 cm. Inner: Average 0.8 cm.
*Apex*.—Acute.
*Base*.—Cuneate.
*Margin*.—Entire, no undulation.
*Texture*.—Outer: Smooth, glabrous, velvety. Inner: Smooth, glabrous, velvety.
*Rugosity*.—Non-rugose.
*Luster*.—Outer: Slightly to moderately glossy. Inner: Matte to slightly glossy.
*Color upper and lower surfaces*.—When opening: Upper side: RHS Red 55B, fading to Red-Purple 68C at base. Under side: RHS Red 55B, fading to Red-Purple 68C at base. Fully opened: Upper side: RHS Red-Purple 68C fading to 68D at base. Under side: RHS Red-Purple 68C fading to 68D at base.

Peduncle:

*Terminal length*.—Average 6.5 cm.
*Terminal diameter*.—0.5 cm at widest, 0.4 cm at narrowest.
*Angle to lateral branch axis*.—Average 45°.
*Strength*.—Moderately strong.
*Texture*.—Glabrous, smooth.
*Luster*.—Moderately glossy.
*Color*.—RHS Yellow-Green 146A.

Pedicel:

*Length*.—Average 1 cm.
*Diameter*.—Average 0.125 cm.
*Angle to lateral branch axis*.—Average 25° to peduncle.
*Strength*.—Moderately weak.
*Texture*.—Glabrous, smooth.
*Luster*.—Moderately glossy.
*Color*.—RHS Red 54D.

Bracts: One pair of concave bracts is present at the base of each ovary.

*Shape*.—Broad ovate, folded.
*Apex*.—Broad acute.
*Margin*.—Entire.
*Base*.—Broad cuneate.
*Length*.—Average 0.9 cm.
*Width*.—Average 0.7 cm.
*Texture*.—Both sides smooth, glabrous, slightly glossy and moderately velvety.
*Color*.—Transparent white; RHS White 155C.

REPRODUCTIVE ORGANS

No androecium present, female flowers only.

Pistil:

*Number*.—Average 3.
*Length*.—Average 0.4 cm.
*Stigma diameter*.—Average 0.4 cm.
*Stigma shape*.—Spiral, cleft in two.
*Stigma color*.—RHS Yellow 12A.
*Style length*.—Average 0.2 cm.
*Style color*.—RHS Yellow 12C.
*Ovary color*.—RHS Yellow-Green 145C, wings Red 55B.
*Ovary size*.—Diameter and height about 0.3 cm.

OTHER CHARACTERISTICS

Seeds and fruits: None observed to date.

Disease/pest resistance: Similar resistance nor susceptibility to normal diseases and pests of *Begonia* has been observed.

Temperature tolerance: Tolerates temperatures up to 35° C. Hardy to USDA zones 10 to 12. Low to moderate tolerance to rain. Low tolerance to wind.

What is claimed is:

1. A new and distinct cultivar of *Begonia* plant named 'EC-BEGO-2305' as herein illustrated and described.

* * * * *